United States Patent

Rosenstatter

[11] Patent Number: 5,846,078
[45] Date of Patent: Dec. 8, 1998

[54] DENTAL ANGULAR INSTRUMENT HOLDER

[76] Inventor: Otto Rosenstatter, Matzing 105, A-5164 Seeham, Austria

[21] Appl. No.: 845,898

[22] Filed: Apr. 28, 1997

[30] Foreign Application Priority Data

May 3, 1996 [DE] Germany .................. 196 17 670.0

[51] Int. Cl.$^6$ ..................................... A61C 1/05
[52] U.S. Cl. ............................................. 433/132
[58] Field of Search ................... 433/114, 120, 433/132, 133; 415/904

[56] References Cited

U.S. PATENT DOCUMENTS

| | | | |
|---|---|---|---|
| 4,171,571 | 10/1979 | Gritter | 433/132 X |
| 4,212,641 | 7/1980 | Eibofner et al. | 433/133 |
| 4,504,227 | 3/1985 | Lohn | 433/132 X |
| 4,568,642 | 2/1986 | DeForrest et al. | 433/132 |
| 5,476,380 | 12/1995 | Rosenstatter | 433/132 X |

*Primary Examiner*—Nicholas D. Lucchesi

[57] ABSTRACT

In a dental angular instrument holder (10) a turbine (142) for driving a clamping chuck (62) for an instrument (64) is installed in a handle part (12) and is supported on a drive shaft (70) passing through a neck part (14). The drive shaft is fixedly connected to the clamping chuck (62) via a 90° direction-changing gear. The turbine (142) can have large radial dimensions, compared to a turbine installed in the working head (16) of the angular instrument holder, so that a greater torque can be exerted on the instrument (64). In addition the movement-changing gear (66, 68) is at the same time designed as a reduction gear.

16 Claims, 3 Drawing Sheets

5,846,078

DENTAL ANGULAR INSTRUMENT HOLDER

BACKGROUND TO THE INVENTION

The present invention relates to a dental angular instrument holder or handpiece.

A dental angular instrument holder might include a handle part, connected to a neck part by an elbow region in such a way that the neck part axis and the handle part axis abut one another at an obtuse angle. It might include a working head provided with a clamping chuck for an instrument, and a turbine engaging the clamping chuck.

In such angular instrument holders the turbine blade wheel is directly connected in a torsionless manner to the clamping chuck for an instrument, and a driving air feed channel extends up to the working head of the angular instrument holder. Such angular instrument holders are easy to handle and manipulate, and also have a good cutting performance.

Professional users are also acquainted with angular instrument holders in which the clamping chuck for the instrument is driven by a miniature electric motor, with the involvement of drive shafts, mounted in the handle part. These angular instrument holders are characterised by a high torque delivered to the instrument, but operate at low speeds.

SUMMARY OF THE INVENTION

The present invention provides a dental angular instrument holder of the type discussed above, in which the turbine is arranged in the elbow region and engages the clamping chuck via a drive shaft passing through the neck part.

The holder of the invention has the advantage that it can provide enhanced cutting performance compared with other instrument holders. In particular, in the angular instrument holder according to the invention, the turbine is mounted in the handle part, and since the latter has larger radial dimensions than the working head can have, the turbine generates a higher torque. The pulling ability and the cutting performance can therefore be improved in the angular instrument holder according to the invention. Furthermore, the working head has radially compact dimensions so that the handling and manipulation of the angular instrument holder by the dentist is unaltered.

Preferably, the drive shaft engages the clamping chuck via direction-reversing gear transmission whose axis is perpendicular to the holding part axis. This has the advantage that the holder can be arranged with the working geometry of a normal angular drill holder.

Preferably, the end of the drive shaft adjacent to the working head is provided with a front face toothing that meshes with a gear ring carried by the clamping chuck. This can provide in a simple way for a change of movement from the neck part axis to a working head axis vertical thereto.

Preferably, the direction-reversing gear transmission at the same time effects a rotational speed reduction. Preferably, the rotational speed reduction is preferably in the range between 1.2:1.0 and 2.0:1.0, especially in the range between 1.3:1.0 and 1.5:1.0. This has the advantage of increasing still further the torque delivered to the working head. Preferably, the turbine projects with a section adjacent to the elbow inside into the end section of the holding part adjacent to the elbow region and in which the turbine blade wheel is immovably mounted on the drive shaft. This construction has the advantage of being mechanically simple.

Preferably, a working space of the turbine in which the turbine blade wheel is located is formed partly in a core part of the handle part and partly in an elbow part forming the elbow region, through which the handle part and neck part are connected to one another. This has the advantage of simplifying assembly or disassembly or both.

Preferably, the turbine is arranged eccentrically with respect to the handle part axis, namely on the outside of the elbow part. This provides additional delivery lines for fluids, light and optionally power to be laid between the handle part and the neck part, at the same time also ensuring the maximum available space for the turbine.

Preferably, the driving air inlet of the turbine is adjacent to the elbow inside, and a driving air feed channel running in the axial direction from the driving air inlet is provided in the core part of the handle part. This has the advantage of providing a compact design and construction.

Preferably, an outlet opening of the turbine is displaced relative to the driving air inlet by an angle of about 270° to 330°, preferably about 300°, viewed in the direction of rotation, and communicates with an axial return air channel that is bounded by the core part of the handle part. This provides for a particularly good efficiency of the turbine.

Preferably, the core part and the elbow part respectively define in their section adjacent to the elbow inside a passage through which an optical fibre bundle extends that runs from a coupling section of the handle part to a light outlet opening adjacent to the working head. This enables light to be guided to a light outlet window adjacent to the working head, without thereby having to reduce the amount of space available for the turbine.

Preferably, the transverse cross-section of the passage in the core part and elbow part is in the form of a sickle or slit curved in the circumferential direction. This can enable a light guide of large effective cross-section to be chosen, the optical fibre bundle being laid in a flat cross-sectional form in the region of the bend or elbow part.

Preferably, the elbow part has in its section adjacent to the elbow inside a spray air line and/or a spray water line. This can enable spray air and/or spray water to be conveyed via the elbow part to the working head without reducing the installation space for the turbine.

Preferably, the elbow part and the core part have on their opposite front faces in the region adjacent to the elbow inside, flush-aligned positioning bores in which a positioning pin engages. This can enable accurate assembly and installation of the neck part and handle part of the angular instrument holder.

Preferably, the drive shaft is carried by bearings of a tubular shaft housing, and one end of the shaft housing is supported in the elbow part and the other end of the shaft housing carries the working head. This can facilitate the assembly, installation and dismantling of the angular instrument holder.

Preferably, the working head has a sleeve section overlapping the free end of the shaft housing, the said sleeve section being screwed onto a thread carried by the shaft housing. This has the advantage of providing simple removal and reinstallation of the working head on the neck part.

Preferably, the elbow part and the working head each has a shoulder, and the two ends of an external housing of substantially truncated conical shape of the neck part are supported on these two shoulders. With this construction, assembly of the instrument holder by screwing the working head onto the shaft housing enables an external housing of the neck part to be positioned and secured in place, determining the external shape of the neck part.

INTRODUCTION TO THE DRAWINGS

FIG. 1 is an axial section through a dental angular instrument holder together with various adapter parts, through which fluid can be supplied and removed, and light can be guided to the angular instrument holder, FIG. 2 is an enlarged view of the angular instrument holder illustrated in FIG. 1, shown in an axial angled sectional plane that is reproduced in FIGS. 3 and 4 through the sectional lines I—I, FIG. 3 is a transverse section through the angular instrument holder illustrated in FIG. 2, along the sectional line III—III shown there, and FIG. 4 is a transverse section through the angular instrument holder illustrated in FIG. 2, along the sectional line IV—IV shown there.

DESCRIPTION OF PREFERRED EMBODIMENTS

Figure 1:
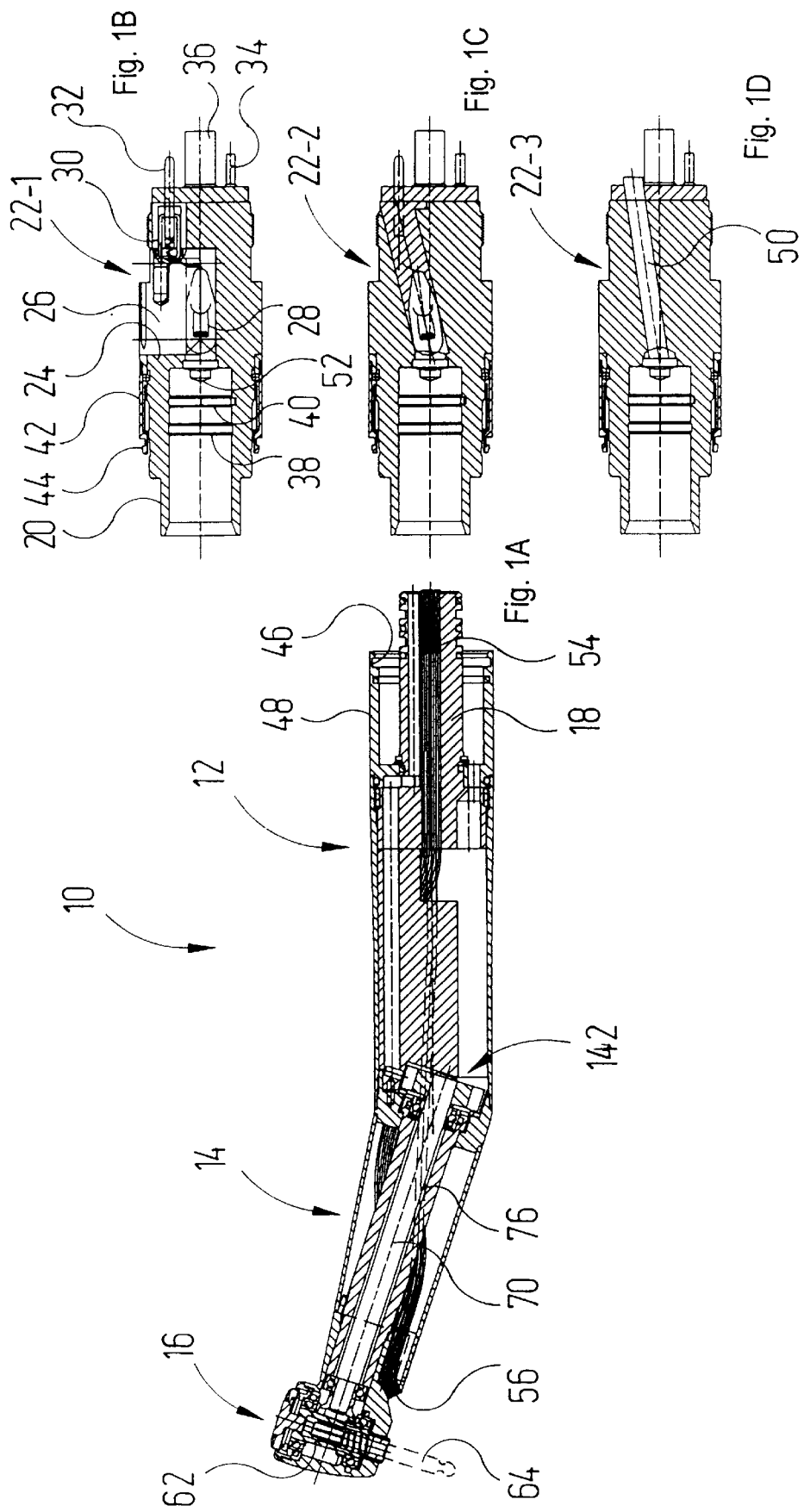

In FIG. 1 an angular instrument holder, generally denoted by the reference numeral 10, has a handle part 12, a neck part 14, as well as a working head 16.

The axis of the neck part 14 is aligned at an obtuse angle to the axis of the handle part 12, and in fact at an angle of about 160° in the embodiment. The abutment between the handle part 12 and neck part 14 thus forms a bend or elbow, whose convexly curved side is also termed the elbow outside in the present description and in the claims, and whose concavely curved side is termed the elbow inside. The axis of the working head 16 is perpendicular to the axis of the neck part 14.

In the right-hand end section in FIG. 1 the handle part 12 has a coupling pin 18 that can be inserted tightly and in a positively engaging manner into a coupling sleeve 20 belonging to an adapter part 22. Three different adapter parts 22-1, 222 and 22-3 are shown in the right-hand part of FIG. 1, which differ in the way and means in which light is transmitted on the axis of the coupling sleeve.

A prism-shaped bulb holder 26 carrying a cold-light bulb 28 is mounted in a radial recess 24 in the adapter part 22-1. The connecting lugs of the bulb 28 are connected via spring-loaded contacts 30 to connecting pins 32, through which current is supplied.

The adapter part 22-1 also has a driving air connection pipe 34 as well as a return air connection pipe 36. Further connection pipes of the adapter part 22, not shown in the drawing, serve to supply spray air and spray water and communicate via channels, also not shown, with annular grooves 38, 40 in the coupling sleeve 20, which grooves in turn communicate with radially terminating end sections (not shown) of channels for spray water and spray air provided in the coupling pin 18.

A retaining sleeve 42 is firmly mounted on the outside of the adapter part 22-1, which sleeve can engage with retaining lugs 44 in a retaining groove 46 that is formed in a control sleeve 48. The latter can rotate, but is fixedly connected in the axial direction to the handle part 12.

In the adapter part 22-2 the bulb holder 26 is formed as a rod-shaped part and the recess 24 is shaped correspondingly like a bore and runs inclined to the axis of the coupling sleeve 20.

In the adapter part 22-3 a light guide 50 is inserted in the recess 24, again formed as a bore, the right-hand front face of the light guide 50 shown in FIG. 1 being in alignment with a light guide of a supply cable when the angular instrument holder is connected in position.

In all three embodiments of the adapter part 22 a lens 52 is arranged on the axis of the coupling sleeve 20, which focuses the light arriving at the axis of the coupling sleeve 20 onto the end of the coupling pin 18. At the end of the said pin is located the free front surface of an optical fibre bundle 54 that leads to a light outlet window 56 of the angular instrument holder adjacent to the working head 16.

Details of the construction of the angular instrument holder 10 will now be described with reference to FIGS. 2 to 4.

A clamping sleeve 62 that can receive and lock in position a shank section of an instrument 64, for example a drill, indicated by broken lines, is mounted in the interior of the working he ad via bearings 58, 60.

The clamping sleeve 62 has a gear ring 66 that meshes with a front face tooth arrangement 68 provided on the free end of an output shaft 70.

The drive shaft 70 is radially and axially mounted via bearings 72, 74 in a tubular shaft housing 76.

Figure 2:
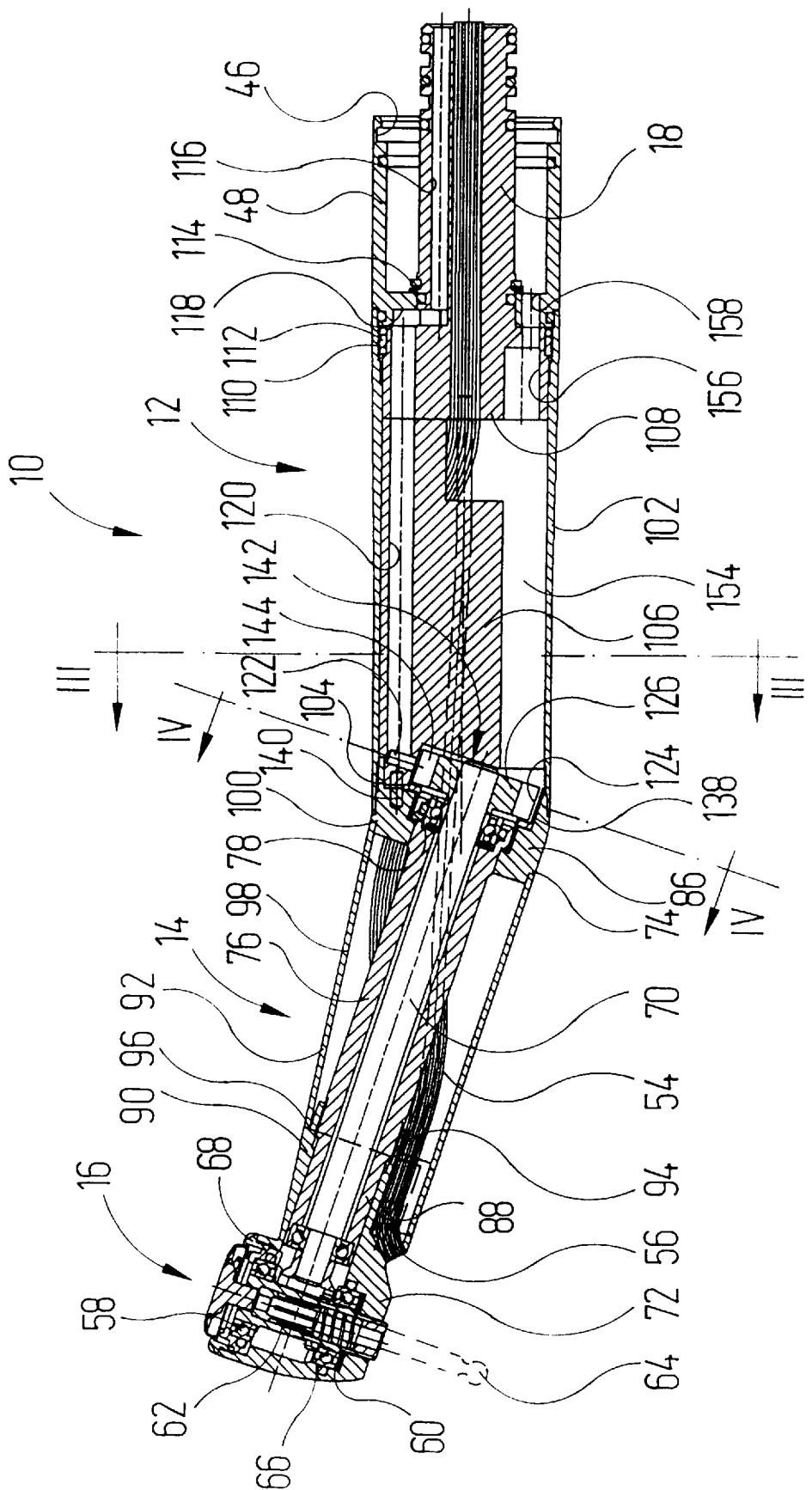

The right-hand end of the shaft housing 76 shown in FIG. 2 is stepped and is supported and engages positively in a stepped counter-bore 78 of an elbow part 86. An end section 88 of the shaft housing 76 of reduced diameter fits tightly in a sleeve section 90 of the working head 16. The sleeve section 90 has at the free end a threaded apron 92 that is screwed onto a threaded section 94 of the shaft housing 76.

The sleeve section 90 of the working head 16 has on its outside a shoulder 96 which supports one end of a truncated conical external housing 98 of the neck part 14. The other end of the external housing 98 rests on a shoulder 100 provided in the left-hand front face of the elbow part 86. When the working head 16 is screwed on, the elbow part 86, shaft housing 76, working head 16 and the outer housing 98, working head 16 and the outer housing 98 are thereby screwed together to form a unit.

The handle part has an external housing 102 that is screwed onto a threaded apron 104 of the elbow part 86 shown on the right in FIG. 2. A core part 106 to which is joined a front face part 108 positively engages in the interior of the external housing 102. The adjacent front faces of the core part 106 and front face part 108 abut one another without any play. The front face part 108 has a shoulder 110 that engages a threaded ring 112 which runs on an internal thread provided on the right-hand end section of the external housing 98.

The coupling pin 18, already described with reference to FIG. 1, is formed on the front face part 108.

The front face of the control sleeve 48 shown on the left in the diagram runs without any play on the annular surface, projecting beyond the coupling pin 18, of the front face part 108 and is secured axially on the coupling pin 18 by means of a snap ring 114.

A driving air channel 116 is provided in an axially parallel manner in the coupling pin 18, which channel communicates via a radial channel section with a control opening 118 formed in the left-hand front face of the control sleeve 48. The control opening 118 can be made to overlap to a greater or lesser extent a driving air channel 120 by appropriately rotating the control sleeve 48, which channel extends through the core part 106 and the front face part 108.

The driving air channel 120 terminates via a tangential inlet channel 122 in a working space 124 in which a turbine blade wheel 126 rotates. The latter is rigidly secured on the drive shaft 70. As can be seen from FIG. 2, the mid-plane of the working space 124 is tilted from a plane transverse to the handle part axis by the obtuse angle enclosed between the neck part axis and the handle part axis. The working space 124 is defined partly by the corresponding design and shape of the left-hand front face of the core part 106 and partly by the corresponding design and shape of the right-hand front face of the elbow part 86. A cup-shaped sheet-metal part 128 encloses the turbine blade wheel 126 and defines the working space 124 through the abutment point between the elbow part 86 and the core part 106.

In order to ensure exact alignment of the elbow part 86 and core part 106, blind bores are provided in the oppositely facing front faces of these parts, into which a positioning pin 140 is likewise inserted.

Figure 4:
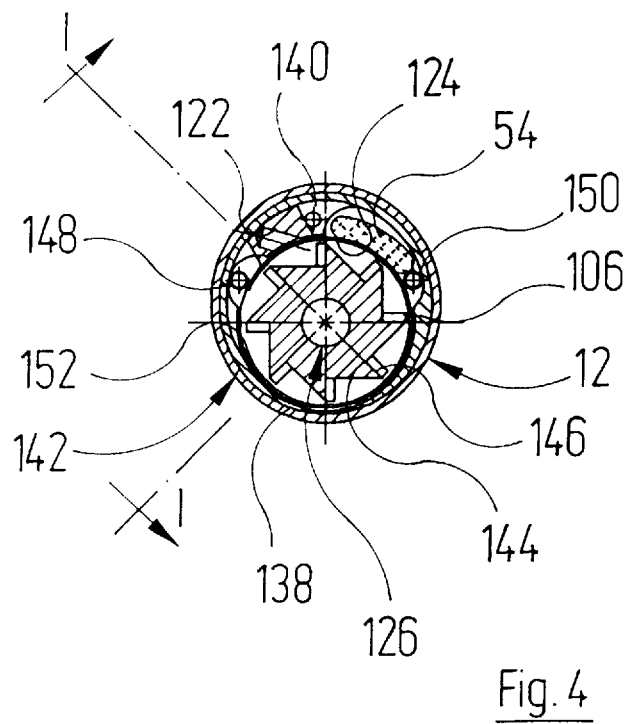

As can be seen from FIG. 4, the turbine formed by the turbine wheel 126 and the working space 124 and generally denoted by the reference numeral 142, is aligned eccentrically with respect to the handle part axis, the diameter of the working space 124 not being substantially less however than the diameter of the handle part 12. In this way the turbine 142 can on account of the enhanced turning moment of the individual turbine blades 144 exert a greater torque than can a turbine mounted directly in the working head 16.

As can also be seen from FIG. 4, the individual blades 144 of the turbine wheel have concave front faces 146 on the side exposed to the flow. This is advantageous as regards a good utilisation of the incident energy.

A passage for the widely laid optical fibre bundle 54 is also provided in the sickle-shaped remaining space of the handle part 12 lying above the working space 124. A spray air line 148 as well as a spray water line 150 also pass through this sickle-shaped space.

As can be seen from FIG. 4, the circumferential wall of the sheet-metal part 138 does not extend a full 360°. An outlet opening 152 for return air under reduced pressure remains between the spaced-apart ends of the circumferential wall of the sheet-metal part 138. This outlet opening encloses an angle of about 300° with the inlet opening formed by the end of the inlet channel 122.

Figure 3:
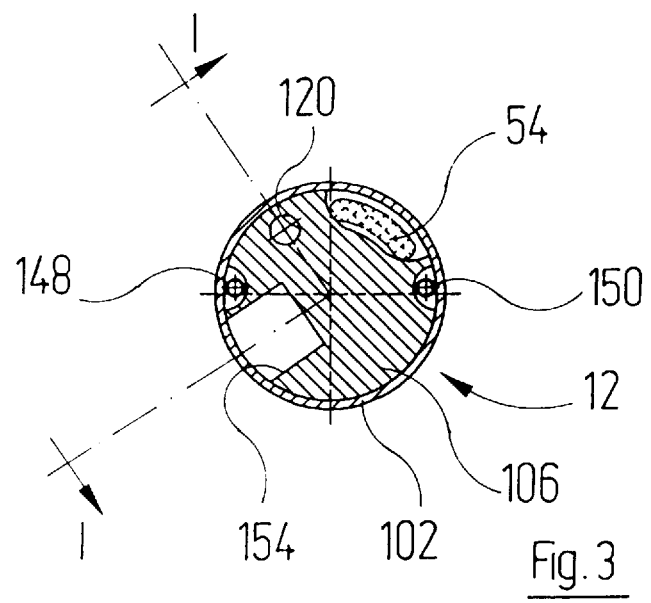

The outlet opening 152 communicates, as can be seen from FIGS. 2 and 3, with a return air channel 154 defined by the core part 106 and the external housing 102. The return air channel 154 communicates with a further return air channel 156 provided in the front face part 108. Its end overlaps to a greater or lesser extent, depending on the angular setting of the control sleeve 48, a further control opening 158 of the said control sleeve 48. The return air under reduced pressure passes from the control opening 158 through the annular space defined by the coupling pin 18 and the control sleeve 48, into a return air channel (not shown in the drawing) of the adapter part 22, and from there to the return air connecting pipe 36.

As has already been discussed above, the described angular instrument holder can generate a higher torque on account of the greater radial dimensions of the turbine 142 compared to conventional turbine-driven angular instrument holders. Furthermore the movement and reversing transmission system that is formed by the gear ring 66 and the front face toothed system 68 is also designed as a reduction gear. The reduction ratio of this gear system is in practice between 1.2:1.0 and 2.0:1.0, preferably 1.3:1.0 to 1.5:1.0.

The described angular instrument holder thus has the same external contour and shape and the same handling and manipulation as a conventional turbine-operated angular instrument holder with the turbine integrated into the working head 16, but can transmit a considerably enhanced torque to the instrument 64.

It is also clear from the above description that it is very easy to install and remove the aforedescribed angular instrument holder.

What is claimed is:

1. A dental angular instrument holder with a handle part, with a neck part and a holding part connected to the handle part by an elbow region in such a way that the neck part axis and the handle part axis abut one another at an obtuse angle, further comprising a working head that is provided with a clamping chuck for an instrument, and with a turbine engaging the clamping chuck, wherein the turbine is arranged in the elbow region and engages the clamping chuck via a drive shaft passing through the neck part.

2. An angular instrument holder as claimed in claim 1, in which the drive shaft engages the clamping chuck via a direction-reversing gear transmission whose axis is perpendicular to the holding part axis.

3. An angular instrument holder as claimed in claim 2, in which the end of the drive shaft adjacent to the working head is provided with a front face toothing that meshes with a gear ring carried by the clamping chuck.

4. An angular instrument holder as claimed in claim 3, in which the direction-reversing gear transmission at the same time effects a rotational speed reduction.

5. An angular instrument holder as claimed in claim 1, in which the turbine projects with a section adjacent to an inside surface of the elbow region into an end section of the holding part adjacent to the elbow region and in which a turbine blade wheel is immovably mounted on the drive shaft.

6. An angular instrument holder as claimed in claim 5, in which a working space of the turbine in which the turbine blade wheel is located is formed partly in a core part of the handle part and partly in an elbow part forming the elbow region, through which the handle part and neck part are connected to one another.

7. An angular instrument holder as claimed in claim 6, in which the turbine is arranged eccentrically with respect to the handle part axis, on the outside of the elbow region.

8. An angular instrument holder as claimed in claim 7, in which a driving air inlet of the turbine is adjacent to the inside surface of the elbow region, and a driving air feed channel running in an axial direction from the driving air inlet is provided in the core part of the handle part.

9. An angular instrument holder as claimed in claim 7, in which an outlet opening of the turbine is displaced relative to a driving air inlet by an angle of about 270° to 330°, viewed in the direction of rotation, and communicates with an axial return air channel that is bounded by the core part of the handle part.

10. An angular instrument holder as claimed in claim 6, in which the core part and the elbow part respectively define in their section adjacent to the inside surface of the elbow region a passage through which an optical fiber bundle extends that runs from a coupling section of the handle part to a light outlet opening adjacent to the working head.

11. An angular instrument holder as claimed in claim 10, in which a transverse cross-section of the passage in the core part and elbow region is in the form of a sickle or slit curved in the circumferential direction.

12. An angular instrument holder as claimed in claim 6, in which the elbow region has in its section adjacent to the inside surface of the elbow region a spray line for at least one of water and air.

13. An angular instrument holder as claimed in claim 6, in which the elbow region and the core part have on their opposite front faces in the region adjacent to the elbow inside, flush-aligned positioning bores in which a positioning pin engages.

14. An angular instrument holder as claimed in claim 6, in which the drive shaft is carried by bearings of a tubular shaft housing, and in which one end of the shaft housing is supported in the elbow region and the other end of the shaft housing carries the working head.

15. An angular instrument holder as claimed in claim 14, in which the working head has a sleeve section overlapping a free end of the shaft housing, the said sleeve section being screwed onto a thread carried by the shaft housing.

16. An angular instrument holder as claimed in claim 15, in which the elbow region and the working head each has a shoulder, and the two ends of an external housing of substantially truncated conical shape of the neck part are supported on these two shoulders.

\* \* \* \* \*